United States Patent [19]

Skidmore, III

[11] 4,111,055
[45] Sep. 5, 1978

[54] PULSE ECHO ULTRASONIC SYSTEM

[75] Inventor: William J. Skidmore, III, Mission Viejo, Calif.

[73] Assignee: Del Mar Avionics, Irvine, Calif.

[21] Appl. No.: 840,733

[22] Filed: Oct. 11, 1977

[51] Int. Cl.² ............................................. G01N 29/00
[52] U.S. Cl. ....................................... 73/620; 73/901;
128/2 V; 358/112
[58] Field of Search ................. 73/606, 607, 618, 620,
73/901; 128/2 V, 2.05 Z; 340/1 R, 3 R, 5 MP;
358/112

[56] References Cited

U.S. PATENT DOCUMENTS 4,010,466  3/1977  Hofstein .............................. 340/3 R

FOREIGN PATENT DOCUMENTS 2,619,684  11/1976  Fed. Rep. of Germany ........... 358/112

OTHER PUBLICATIONS

Chow et al., "Digital Processor for Data Compaction and Image Enhancement of Echo Graphical Signals," IBM Tech. Disclosure Bulletin, vol. 17, No. 10, pp. 3154–3158, Mar. 1975.

Primary Examiner—Stephen A. Kreitman
Attorney, Agent, or Firm—Keith D. Beecher

[57] ABSTRACT

A pulse echo ultrasonic system is provided for medical diagnosis, and the like, which has particular application to echocardiography, and which includes a digital memory for presenting a rolling dynamic display in shades of gray on the screen of a cathode-ray tube scanned in accordance with present-day television standards, and which may be interfaced with present-day video tape recorders. The system of the invention involves a time extrapolating function which serves to expand the effective memory capacity when used in a selective mode applicable to echocardiography, and certain other bio-medical areas, such as scintillation camera displays, and other radiographic displays used in the area of medicine.

7 Claims, 5 Drawing Figures

PULSE ECHO ULTRASONIC SYSTEM

BACKGROUND OF THE INVENTION

Pulse echo ultrasonic systems are known to the art which use ultrasound to identify and discriminate structures within the human body for the purposes of medical diagnosis. Echocardiography is a diagnostic technique which uses such pulse echo system to visualize the heart of a living patient without actually invading the body of the patient.

By definition ultrasound is sound having a frequency above 20 KHz, that is, above the audible range. Actually, ultrasound frequencies in the megahertz range are used for medical diagnostic purposes. The principal features which make ultrasound useful as a diagnostic instrument are that ultrasound, as compared with audible sound, can more easily be directed as a beam, it more easily obeys the laws of reflection and refraction whereby the wavelength $\lambda$ determines the theoretical resolution; and it is reflected by objects of very small size. Since it is virtually impossible for ultrasound to pass into the body of a patient from the ambient air, the transducer producing the ultrasound must have an airless contact with the body, and use a suitable couplant.

The development of ultrasonic pulse echo systems has become practical with the development of piezoelectric transducers. Such transducers produce sound waves when activated by an electric field, and produce electric impulses when impacted by a sound wave. The usual prior art ultrasonic pulse echo system includes a piezoelectric transducer which is placed in airless contact with the body of the patient, and which introduces ultrasonic frequency bursts, or pulses, of ultrasound into the body of the patient in response to corresponding electric pulses from a transmitter; and which receives bursts, or pulses, of ultrasound echos and converts the echos into corresponding electric impulses which are introduced to a receiver. The transmitter includes appropriate circuitry which excites the transducer at its resonant frequency for an output burst "main bang" of radio frequency ultrasound energy, at a given repetition rate. The receiver includes appropriate processing circuitry for converting the electric echo impulses from the transducer into an appropriate display on the screen of a cathode-ray tube.

Since the electric energy is intermittently fed into the transducer, the transducer emits bursts of ultrasound for very brief periods of time. The duration of each ultrasonic impulse "main bang" may be approximately 1 microsecond for a 2.25 MHz transducer. Following the emission of a burst of ultrasound, the transducer awaits the reception of any reflected ultrasound echo impulses for a period of time dependent on the tissue depth being examined. After a relatively long period of time, or dwell time, another burst of ultrasound is emitted and the cycle is repeated. The rate at which the bursts of ultrasonic energy are emitted by the transducer is the repetition rate of the system. Commercial diagnostic echocardiograph systems have repetition rates in the general area of from 200–2000 per second. A commonly used echocardiograph system has a 1 microsecond burst of ultrasound with a repetition rate of 1,000 per second, with a transducer of 2.25 MHz.

If the interface from which the echo is reflected is constantly moving, then the echo position will change constantly with respect to the transducer. One of the present-day accepted techniques for displaying echo motion for echocardiography systems is intensity modulation of the cathode-ray beam (TM-scan) which is typically scanned vertically across the screen of the cathode-ray tube from top to bottom, whereby the horizontal sweep rate selects the desired number of cardiac cycles. The amplitude of the echo determines the specific intensity of gray shade. That is, the greater the amplitude of the echo, the brighter the resulting dot on the screen of the cathode-ray tube, this relationship is usually established with a non-linear transfer function for gamma correction of the display used.

A primary objective of the present invention is to provide a TM-scan echocardiograph system of the type described above which is capable of presenting a dynamic rolling bright gray-scale display on the screen of a cathode-ray tube which is scanned, for example, on a standard 525-line television format. This is achieved by incorporating a digital semiconductor memory into the system, and of providing circuitry whereby the capacity of a given sized digital memory or other type of digital memory, may be greatly expanded, in accordance with the teachings of the present invention.

In the television system presently used in the United States, 30 picture frames are transmitted every second. Each frame is divided into two interlaced fields referred to as the odd field and the even field. Each frame comprises 525 horizontal lines or traces, so that each field comprises $262\frac{1}{2}$ lines. During each field the cathode-ray beam in the television picture tube is swept from left to right producing a horizontal line, the beam is then blanked and retraced for the next line which is produced at a position two lines below the preceding line. This action continues until the bottom of the picture screen is reached. The beam is then blanked and retraced to the top of the screen and then proceeds to trace out the even field which is interlaced with the odd field.

The use of ultrasonic pulse echo systems is gaining wide acceptance in the cardiology art. While most prior art echocardiograph systems yield meaningful diagnostic information, the capability for presenting a dynamic rolling bright gray-scale TM display on a standard 525-line television format is not currently available. Scan conversion memories do provide a bright gray-scale display, but are unable to present a dynamic rolling display, and have limited retention abilities. This capability is important since the resulting display has the same flexibility as the now familiar electrocardiograph. It is, accordingly, an objective of this invention to provide an improved system for the implementation of a digital monolithic memory or other digital memory means for presenting a rolling dynamic display on a standard 525-line format television screen, which may be directly interfaced with any standard video recorder.

Diagnostic ultrasound techniques are routinely used in physiological areas. Although the ultrasonic pulse echo equipment being used in all cases is almost identical in operational capabilities, one major variation is evident in the case of echocardiograph systems. This variation concerns the manner in which returning echo groups from the heart are processed, and concerns the passing of the demodulated echo groups through a single pole high-pass filter, or equivalent filter, which has characteristically a nominal 6 db/per octave roll-off from the break frequency. The significance of this simple network for markedly improving the end performance is the fact that lower frequency components are sufficiently attenuated in the demodulated echo groups, so as to be negated from the time motion display. Consequently, the direct implication is that detection of higher frequency information in demodulated echo groups of 700 KHz bandwith for a 2.25 MHz transducer carries sufficient information for echocardiograph display purposes, and more importantly, this is a desired condition for optimized performance. This feature is utilized in the echocardiograph system to be described, and forms the basis for the extrapolation expanded memory concept of the invention.

The system to be described involves the following ultrasound physiological resolution and digitization considerations: an ultrasound system has a theoretical upper resolution limit defined by the wavelength $\lambda$, of the ultrasound frequency being propagated through the tissue. For echocardiography work, the most widely used transducer frequency is 2.25 MHz. The average velocity used for biological studies is 1540 meters per second. The main factor which mitigates this value is the "Q" of the transducer itself which lowers the resolution from a theoretical resolution of 0.6844 mm for a 2.25 MHz transduer to 1.5 to 2 mm whereby effects from phasing cancellation are relatively non-existent for the 2 mm resolution measurements. While probes can be designed with lower Q's, the optimization between resolution and sensitivity dictates the higher Q device for commercially available or practical systems.

Echos received by the transducer are time gain controlled amplified, demodulated, and differentiated, prior to digitizing in the system of the invention. A physiological resolution of 1.5 mm requires a period of 1.33 microseconds between demodulated echo group peaks. An amplifier with a 500 nanosecond rise time is able to duplicate this response since the upper frequency is basically (0.35)/Tr. Digitization of the echo is accomplished in a hypothetical system by using a sampling frequency at least 3 times greater than 700 KHz, which is the step response of the amplifier. Taking 512 samples during the maximum period of 240 microseconds establishes a sampling frequency of 2.13 MHz. This would normally require a digital memory of 512 × 512 × 4 (16 levels of gray) or 1,048,576 bits to provide information for one interlaced 525-line television frame.

A modification of the system to be described may involve the following television resolution considerations: the 525-line television format dictates that for maximum presentation detail, the time motion echo information be stored in a two-dimensional memory matrix. This is due to the characteristics of the television vertical and horizontal resolution. The horizontal resolution is a function of the video response, by which eighty television line pairs may be properly resolved for each megahertz of video bandwidth. A television line pair is defined as alternate black and white lines, representing maximum and minimum video information. Available commercial video recorders exhibit video bandwidths from 2 MHz to 3 MHz, or greater, for black and white recording. One commercial video recorder (Sanyo/VTR-1375) specifies a bandwidth of 3.5 MHz — 14 db down with a horizontal resolution of 300 lines. The vertical resolution is 525 lines with 40 lines used for vertical retrace, so that 485 lines are actually available in normal system usage.

The television camera in the modified system degrades the usual vertical resolution by another factor of 0.7, due to the fact that a horizontal line in the scene may be registered by the camera on one or possibly two adjacent scan lines with a statistical uncertainty. Since digital circuitry is used in the system of the invention, this additional degradation will not be encountered. The horizontal resolution will typically be 38% less than the vertical resolution when using even a good quality video recorder.

In presenting a rolling display by the system of the invention, a constant number of echo reception periods or "main bangs" will be established for whatever roll cycle is required, which may take from 0.5 to 8 seconds. A roll cycle is defined as the length of time for display information to progress from one edge to the other of the television display screen by convention from left to right. The memory of the system has a fixed capacity requirement regardless of the roll rate, since echo input data rate varies as a function of the roll cycle rate. The memory is read in a cyclic mode with an incremental shift in each television field to the first-in line in the television display which is refreshed by new echo data. The system of the present invention uses time extrapolation to expand significantly the specific memory capacity when used in a selective mode applicable to echocardiography, and other bio-medical display applications.

The application of digital memories for various types of displays are presently in wide use. Computer display terminals, and various types of medical products, such as scintillation scanners, etc., utilize the advantages of digital monolithic memories. The main constraint, however, of digital memories for many commercial products has simply been an economic consideration Therefore, it is significant that the system of the present invention is capable of utilizing a given memory capacity with much greater efficiency, than comparable systems in the prior art.

The time extrapolated echocardiograph system of the present invention can best be understood by examining the following example in one of its possible forms, which involves the use of six-bit words, whereby the first four bits constitute a binary word determining the peak amplitude, and the last two bits constitute another binary word determining time position. Four bits of each word are utilized in the normal manner for determining gray-scale in 15 levels of gray and one level of zero amplitude (pixel). The fifth and sixth bit (time extrapolation bits) are used for the determination in which of the four intervals of a sample period the peak of a particular pixel is to be presented. When the pixel is presented, it is reconstructed as a function of amplitude. A delay is required to reconstruct the leading edge of the echo. The four intervals of the sample period refer to the first, second, third, and fourth quarter of the sample period. Statistically, the worst case error occurs within the period of the portion of the selected interval period as determined by the time extrapolation bit(s). It should be noted that only one pixel (picture element) peak can be presented during a sample period while reconstruction techniques allow for overlap. This memory technique enables a specific pixel to be positioned within the sample period interval with an accuracy of four times (two extrapolation bits) the sampling frequency being used. This fact greatly reduces the memory required since less storage is necessary. It will become apparent to those skilled in the state of the art that other combinations may be readily achieved by increasing or decreasing the magnitude of the binary word governing both the peak amplitude, and/or the number of divisions of the sample period.

For echocardiograph information to be digitally recorded, a sampling frequency of at least 2.1 MHz must be used for reproducing demodulated echo groups with a bandwidth of about 700 KHz. Since echo information typically occurs for a maximum of 240 microseconds, no less than 504 samples, and typically 512 ($2^9$) (an even digital increment), must be utilized so as to assure the 700 KHz bandwidth. Now, if 256 lines are to be recorded with adequate video bandwidth in a digital memory, the total memory for two television fields, or one frame, is 512 × 512 × 4 (16 levels of gray) or roughly 1,048,576 bits. It should be noted that not less than 1.5 times the Nyquist sampling theorem or 3 times the desired frequency can be practically utilized without serious affecting or limiting frequency response and presenting aliasing problems. The 700 IHz echo response is necessary for defining the required physiological accuracy of approximately 1.5 mm using a transducer frequency up to 2.25 MHz.

For the extrapolation expanded memory of the system of the invention, with a physiological accuracy of 1.5 mm using a 2.25 MHz transducer, a sampling frequency of 533 KHz is required for 1.44 mm of physiological resolution. This uses 128 samples during a 240 microsecond period. The memory required is 512 × 128 × 6, or 393,216 bits, whereby four-bits yields 16 levels of gray shade, and the last two bits ($2^4$) and $2^5$) are used for time extrapolation. This represents a 62½ percent reduction in memory, as well as in main memory cost, for a system with up to a 2.25 MHz transducer frequency. For systems requiring the usage of higher frequency transducers, the sampling frequency must be increased whereby the ratio between the extrapolation expanded memory and the standard memory remains constant for a given extrapolation power.

The first prerequisite to the operation of the extrapolation expanded memory system of the invention is the detection of peak information in the echo groups, and the determination of the occurrence of this information with respect to the beginning of each consecutive sample period occurring during an echo reception period. High speed TTL Schottky logic may readily be used for this determination, whereby the two extrapolation bits will both be set to "0" if the peak information occurs during the first quarter, a "1" and "0" for the second quarter, a "0" and "1" for the third quarter, and both 1's if the peak information is present during the last quarter. The circuit complexity and cost for this function is minimal and encompasses standard design criteria.

The memory organization for one possible configuration is given. A two-field partitioned memory plane architecture, using 16 K dynamic random access memories, will be described. Such an organization consists of two 32 K × 6 memory planes, whereby two six-bit words may be written or read in parallel within a memory cycle, where each six-bit word includes peak amplitude and time extrapolation information. Encoded extrapolation bit(s), and the encoded peak amplitude information bits are jointly utilized in a special reconstruction algorithm, whereby synthesized echos are generated which mimic the original echos, but have improved characteristics for display purposes, whereby the relationship between the base period of the echo to peak amplitude of said echo, may readily be changed, programmed or altered for echos of different peak amplitudes, whereby reconstructed echos may be linearly or'ed, or may be algebraically added.

To establish compatibility with the television display, synthesized echos are reconstructed from the main memory with a time scaling factor of approximately 4.8 × real time. For an ultrasound reception period of 240 μsec., this period must be compressed to within about 50 μsec., for the writing of one television horizontal line, flyback time increases the total period of time to about 63.5 microseconds.

DETAILED DESCRIPTION OF THE ILLUSTRATED EMBODIMENT

Figure 1:
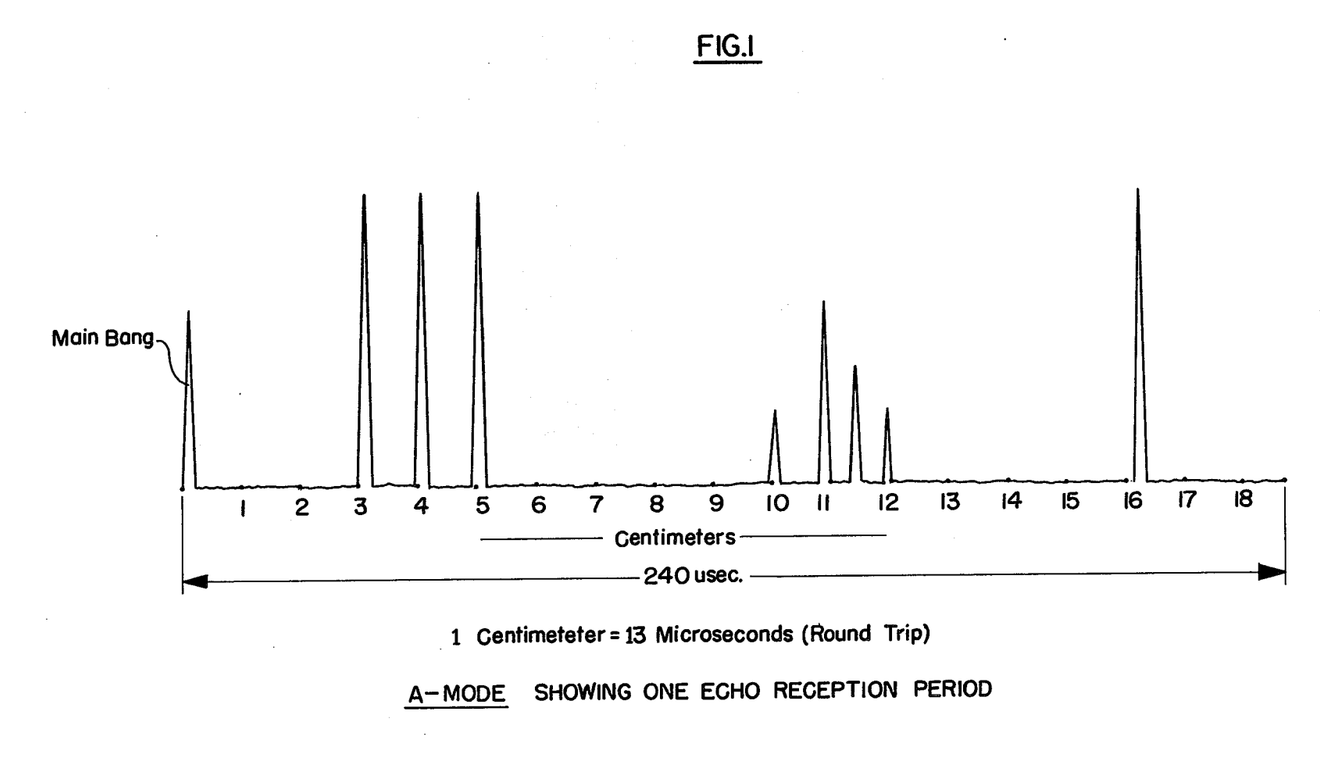
FIG. 1 is a representation of an A-scan echocardiograph display.

FIG. 1 represents one line of echo data as viewed on the screen of a typical prior art A-scan cathode-ray tube in a prior art pulse echo ultrasonic system. As the cathode-ray beam scans across the screen of the tube, the initial pulse from the transmitter, designated the "main bang", which is transmitted into the body occurs to the left of the screen, and the various echo pulses occur as vertical deflections, as the beam is scanned horizontally across the screen. In a usual prior art display, the line of echo data corresponds to 240 microseconds, and each centimeter across the screen represents an echo round trip of 13 microseconds. This follows because if one knows the velocity of sound travelling through the medium being examined, as well as the time it takes for the ultrasound to leave the transducer, strike the interface and return as an echo, it is then a simple matter to calculate the distance of the reflecting interface from the transducer.

By calibrating the screen of the A-scan echo graph for the velocity of sound in the medium being examined, the conversion of time to distance may be accomplished automatically. Thus, instead of indicating how long it takes for a burst of ultrasound to leave the transducer and return as an echo, the electrical signal generated by the returning echo is actually displayed on the screen of the cathode-ray tube as being a certain distance away from the transducer.

If the interface from which the echo is derived is constantly moving, then the echo position will change constantly with reference to the transducer on the A-scan of FIG. 1. The motion could be recorded by taking a moving picture of the face of the cathode-ray tube. However, the A-scan type of display is not very practical for moving echos because the frequency response is limited to the speed of the movie camera, and the movie projector is also necessary to review the data. A better technique for display echo motion is intensity modulation, known as TM-scan or M-scan. This type of modification converts the amplitude of the echo into intensity, and the signal is used to modulate the intensity of the cathode-ray beam, so that the display is converted from a spike to a dot. Within limits, the taller the echo, the brighter the dot. The system of the present invention is concerned with a TM-scan type of echocardiograph system and, as mentioned above, the system includes a digital memory for presenting a rolling dynamic display on the screen of a cathode-ray tube scanned in accordance with present-day television standards, and which may be interfaced with present-day video tape recorders.

Figure 2A:
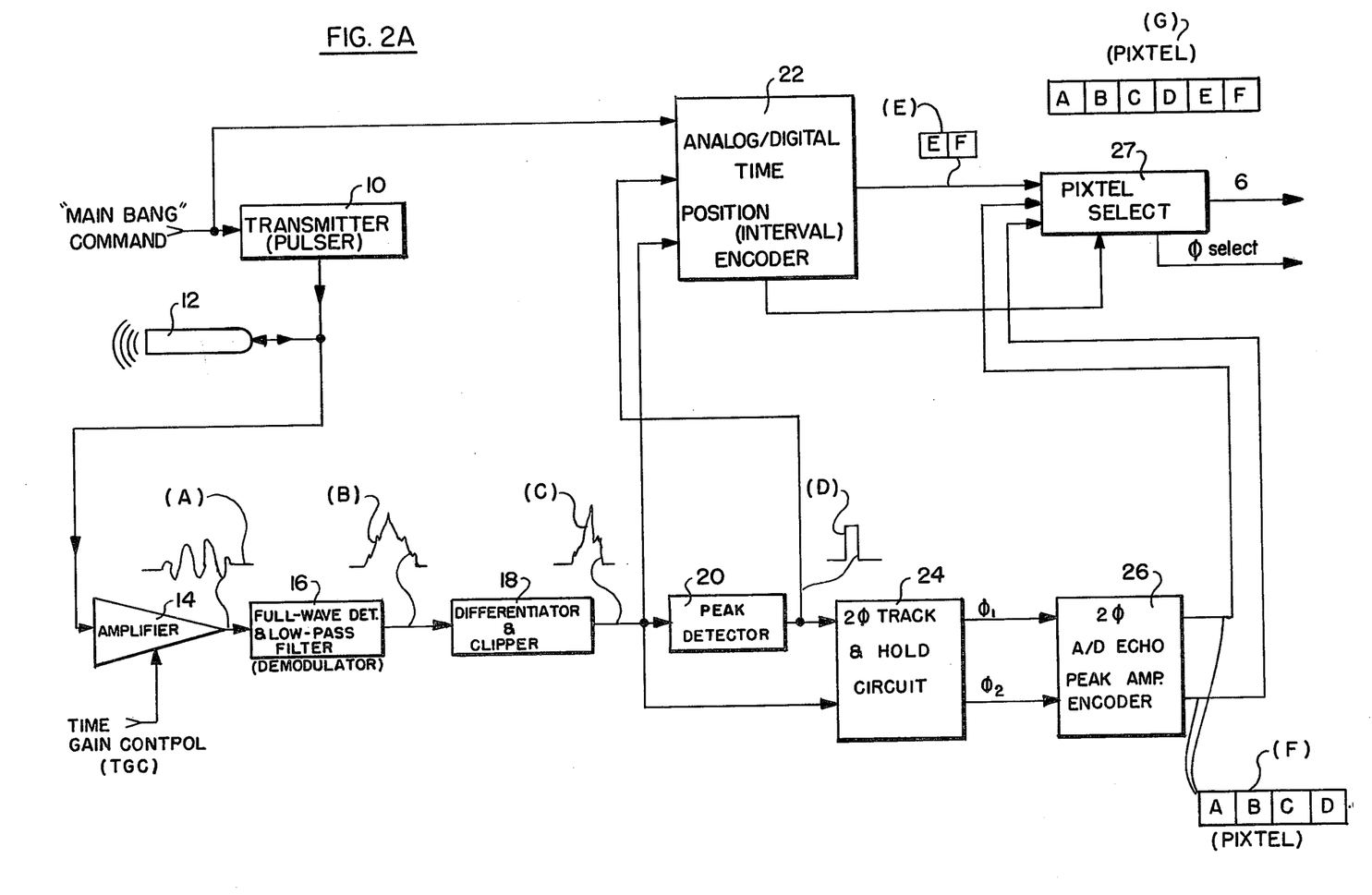
FIGS. 2A and 2B represent a block diagram of an echocardiograph system involving the concepts of the present invention.
Figure 2B:
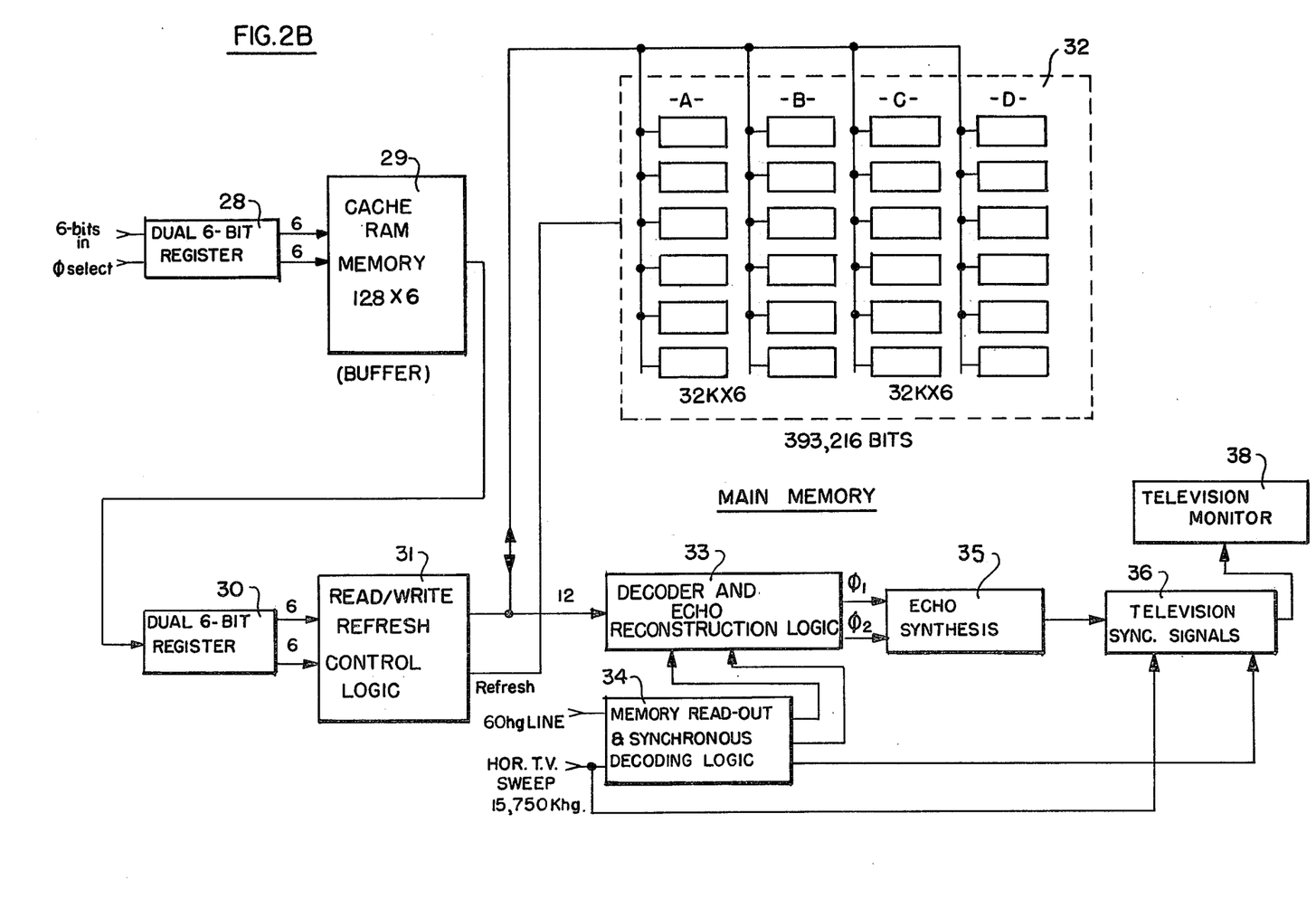

In the block diagram of FIGS. 2A and 2B, a transmitter 10 is used to activate a transducer 12, so as to cause the transducer to emit ultrasound pulses into the body of the patient at predetermined intervals. The echo pulses received by the transducer are amplified in an amplifier 14 which may be time gain controlled, in accordance with known techniques. The resulting radio frequency echo pulses (A) are demodulated in a demodulator 16 which includes, for example, a full-wave detector and a low-pass filter. The filter may be a Butterworth six-pole 700 KHz low-pass filter. The resulting demodulated pulse (B) corresponding to each received echo pulse, is differentiated and clipped in a differentiator and clipper circuit 18, which produces peaked differentiated pulses (C). The pulses (C) are detected in a peak detector circuit 20 which provides an output pulse corresponding to the peak amplitude of the differentiated pulses (C) and selects the peak of greatest amplitude occurring during a sample period. The output pulses (D) from the peak detector 20 are applied to an analog-digital time position encoder 22, and to a $2\phi$ track and hold circuit 24, whereby the peak of every other echo is respectively maintained on each of the outputs.

Figure 3:
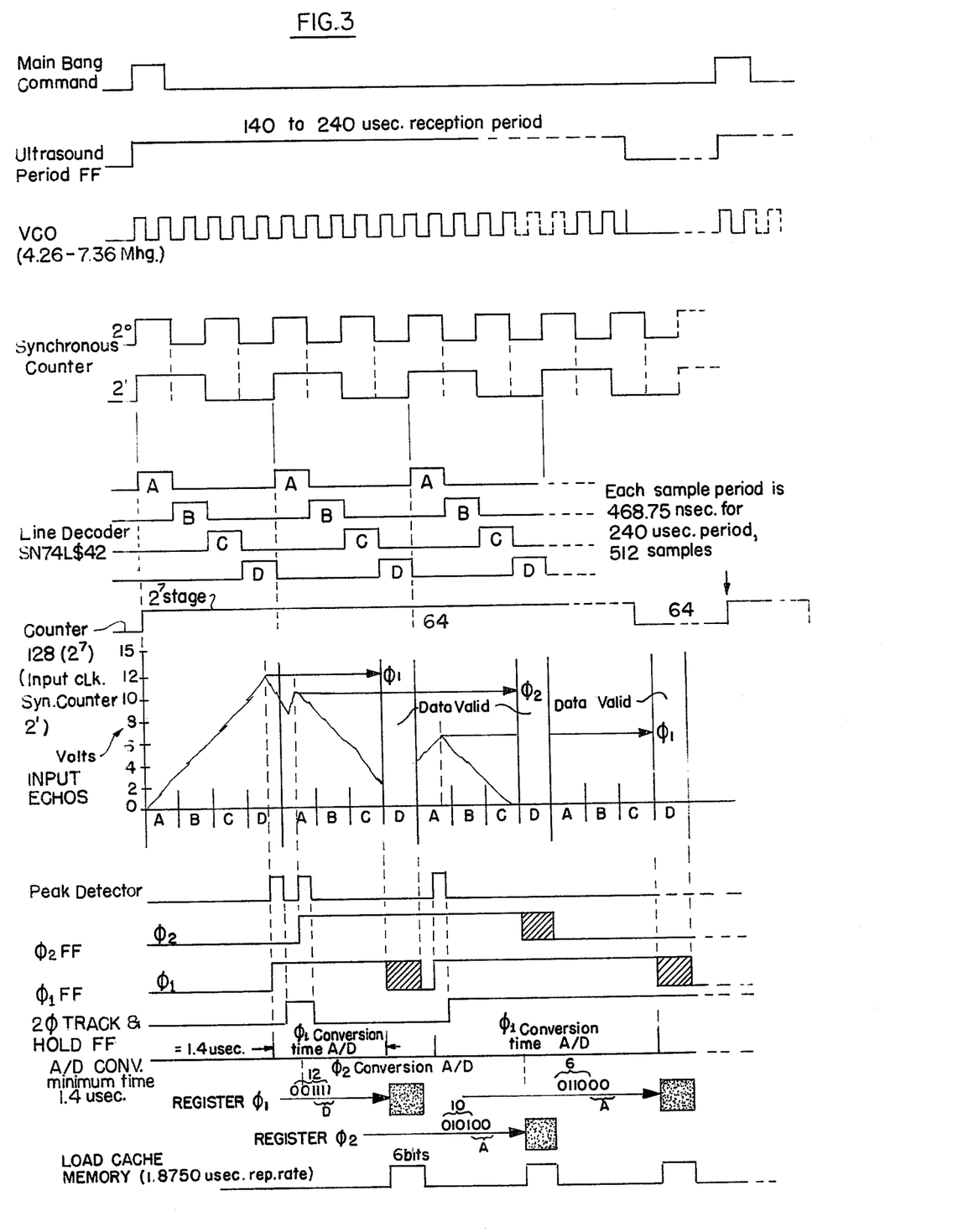
FIGS. 3 and 4 are logic flow diagrams useful in explaining the operation of the various components and functions of the system of the invention.

The analog-digital time position encoder 22 is enabled by the "main bang" command, which starts a voltage controlled oscillator (VCO) with a range of from 4.26 to 7.36 MHz for various echo periods. A counter disables the VCO after 512 cycles. A synchronous mod-four counter and line decoder establishes a sequential succession of positions, A through D, during the echo reception period, such as shown by the logic flow diagram of FIG. 3, with each sample period being divided into four positions or sections. The encoder 22 determines which of the four sections the pulse (D) from peak detector 20 occurs, and it generates a two-bit digital signal which represents digitally an indication of which of the four sections of the sample period in which the pulse (D) occurred. This digital indication is designated (E).

The pulse (D) from the peak detector 20, alternately activates a $2\phi$ track and hold circuit 24, which provides two outputs to the $2\phi$ analog-digital encoder 26 representative of the peak amplitude of the pulse (C). Encoder 26 converts these inputs into corresponding four-bit digital binary words designated (F), and which is commonly known as a "pixel". The digital outputs (E) and (F) are combined to form a digital word of six-bits which will be designated herein as a "pixtel" which represents a combined "pixel" (picture element) and time information. Each pixtel (G) from the encoders 22 and 26 are introduced to 27 the pixtel select circuit, which alternately loads two six-bit registers 28 into 29 a random access memory capable of storing one line of echo reception data. Therefore, all the pixtel words derived from a line of echo data are sequentially stored in buffer 29. This buffer memory is capable of storing 128 six-bit pixtel words, and serves to load the main memory during the dwell cycle preceding the next ultrasonic reception period (main bang).

The pixtel words stored in buffer 29 are serially loaded in pairs into a dual six-bit register 30, and each pixtel pair in register 30 is parallel loaded into the main random access memory (RAM) matrix 32, through the read/write control logic 31. The (RAM) matrix 32 has four rows of memory cells, with six columns. One of the pair of pixtel words from register 30 is loaded into row A, with its bits extending across the six columns, and the other pixtel of the pair is loaded into row B of (RAM) matrix 32, with its bits extending across the columns of row B. Read/write control logic 31 selects the proper memory plane for odd or even television fields and supplies refresh logic for dynamic rams as well as sequential scanning addressing for read and write operations. This circuit also provides for a frozen or still frame or rolling display.

In accordance with the concept of the present invention, as related to the specific embodiment of FIGS. 2A and 2B, each pixtel word contains encoded video information for one ultrasonic echo which is compatible with a conventional television display when reconstructed. The (RAM) matrix 32 stores, therefore, a number of pixtels corresponding to one television frame of information equivalent to the number of pixels required for 512 sample periods for 512 lines. The pixtel words are stored in rows A, B, C and D, so that all the pixtels in rows A and B may be first selected from memory to constitute the odd field of an interlaced television frame, and all the pixtels of rows C and D may then be selected to constitute the even field.

The pixtel words derived from matrix 32, consisting of two parallel six-bit words, are read out at a rate sufficient for reconstructing one echo reception period within 50 microseconds or less, which is the usable display period of one horizontal television line. This is accomplished, referring to FIG. 4, whereby the decoder and echo reconstruction logic block 33 receives parallel six-bit words from matrix 32, while the memory read-out and synchronous decoding logic 34 provides control logic for 33. Circuit 34 consists of a 40.95 MHz clock synced to the horizontal television sweep frequency and counted down by a synchronous four-bit counter, with a line decoder on the two most significant bits of the binary counter. This circuit generates synchronized logic commands and timing interval outputs for memory read-out of 32, and positional interval information of A, B, C and D during the read-out of sample periods for the echo reconstruction logic in 33. Time extrapolation bits E and F, from the appropriate pixtel are compared in 33 with the binary counter bits $2^2$ and $2^3$ in 34, when the magnitude comparator in 33 yields an A=B output a reconstruction echo sequence is initiated by 33. This sequence entails the enabling of one of two count-down binary counters toggled by the 40.95 MHz clock starting with the next sequential positional interval, concurrently the first four-bits of the pixtel; A, B, C and D are compared with the output binary word from the down counter binary counter. When an equality is detected (other than all 0's), one integrator enable of a $2\phi$ integrator command system is activated. This period is active until the binary down counter steps to a low logic level on the carry-out position denoting one cycle of the counter.

Figure 4:
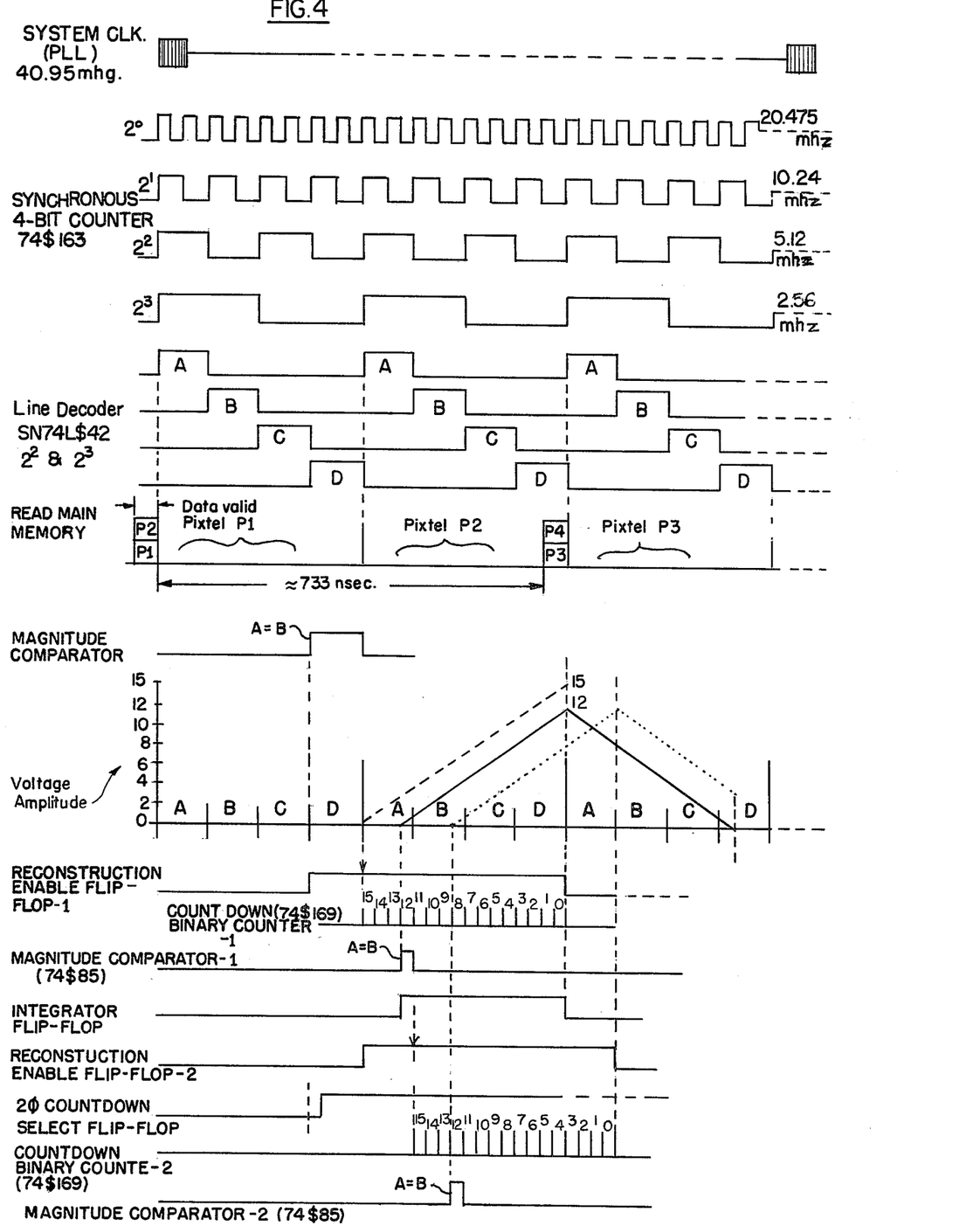

Integrator $2\phi$ commands are fed from 33 to the echo synthesis circuit 35. Four integrators are contained in 35, each integrator has the characteristic that when enabled, integration occurs at a constant rate generating a constant slope ramp, and upon termination of the enable command returns to baseline with equal symmetry. The relationship is now established whereby the binary down counter counts 16 intervals within four positional intervals, and except for the 0 count position which disables the integrator command, can initiate an integrator start command for 15 different positions, resulting in 15 different amplitudes directly correlated to the binary four-bit word; $2^0$, $2^1$, $2^2$ and $2^3$ contained in the pixtel. Four integrators required in 35, to enable overlap of synthesized echos. Multiplexing of four integrators to the 2φ drive lines from 33 is enabled by the drive period requirements for a single echo. Filtering is not required of the reconstructed echos because of the synthesis utilized, circuit 35 allows outputs from all integrators to be or'ed, or summed, or a combination thereof. The output of 35 goes to 36, whereby television synchronization signals are added to the raw video, with the output of 36 yielding a composite standard television video signal compatible with E.I.A. standard specifications. A television closed circuit receiver accepting composite synced video signals 38, may be utilized as well as video recorders.

The invention provides, therefore, a pulse echo ultrasonic system which is particularly suited for medical diagnosis, and which has particular application to echocardiography. The system of the invention, as described above, includes a digital memory for presenting a rolling dynamic display in shades of gray on the screen of a cathode-ray tube scanned in accordance with present-day television standards. The generated composite synchronized signal may be interfaced with present-day video tape recorders. The system of the invention, as described, involves a time extrapolating function which serves to provide adequate system operation with approximately a 63% reduction in memory capacity, over the utilization of standard memory techniques.

The concepts of the present invention enable a high resolution pulse echo ultrasonic system to be produced with a minimum of complexity, and by the use of readily available commercial memories of relatively low densities.

While a particular embodiment of the invention has been shown and described, modifications may be made. It is intended in the claims to cover all modifications which come within the spirit and scope of the invention.

What is claimed is:

1. In an ultrasonic echo system which includes a transmitter, an ultrasonic transducer connected to the transmitter, a receiver coupled to the transducer for receiving echo pulses therefrom, and a television monitor coupled to the receiver, said receiver including: an analog-digital time position encoder for producing a first digital signal representing the time position of the peak amplitude of each received echo pulse within a predetermined sample period; an analog-digital peak amplitude encoder for producing a second digital signal representing the peak amplitude of each of said received echo pulses; digital memory means storing multi-bit digital words representing different gray levels; means coupled to the time position encoder and to the peak amplitude encoder for introducing the first and second digital signals therefrom as multi-bit words to the digital memory means; and means for deriving a plurality of multi-bit words from the digital memory means representing different gray levels in response to each such multi-bit word introduced to said digital memory means.

2. In the system of claim 1, and which includes further memory means for storing the multi-bit words prior to their being introduced to said digital memory means.

3. In the system of claim 1, in which said receiver further includes an amplifier for amplifying radio frequency echo pulses received from the transducer; a detector coupled to the amplifier for demodulating the amplified radio frequency echo pulses from the amplifier; a differentiator coupled to the detector for differentiating the demodulated echo pulse from the detector; a peak detector coupled to the differentiator for producing a pulse corresponding in phase and amplitude to the peak amplitude of each of the differentiated echo pulses from the differentiator; and in which said time position encoder and said peak amplitude encoder are coupled to the output of the peak detector.

4. In the system defined in claim 2, in which said further memory means comprises a random access memory matrix having two sections; and in which said receiver includes register means coupled to the time position encoder and to the peak amplitude encoder for introducing the digital signals therefrom as multi-bit digital words alternately into a first section and into a second section of the further memory means.

5. In the system defined in claim 1, and in which said digital memory means comprises a random access memory having a plurality of memory cells to be selectively addressed by digital signals derived from the further memory means.

6. In the system of claim 3, in which said peak amplitude encoder is a two-phase circuit, and which includes a two-phase track and hold circuit interposed between said peak detector and said two-phase peak amplitude encoder.

7. In the system defined in claim 4, and which includes buffer means interposed between the aforesaid encoders and said register means.

* * * * *